USOO5750751A

United States Patent [19]
Saam

[11] Patent Number: 5,750,751
[45] Date of Patent: May 12, 1998

[54] GLYCOL CO-ESTERS OF DRYING-OIL FATTY ACIDS AND VINYL CARBOXYLIC ACIDS MADE VIA BIPHASIC CATALYSIS AND RESULTING PRODUCTS

[75] Inventor: John C. Saam, Midland, Mich.

[73] Assignee: Michigan Molecular Institute, Midland, Mich.

[21] Appl. No.: 740,700

[22] Filed: Nov. 1, 1996

Related U.S. Application Data

[60] Provisional application No. 60/006,132 Nov. 2, 1995, 60/007,798 Nov. 30, 1995, and 60/008,896 Dec. 19, 1995.

[51] Int. Cl.$^6$ .......................... C07C 67/00; C07C 69/58
[52] U.S. Cl. .................................................. 554/165
[58] Field of Search ............................ 560/224, 225; 554/165

[56] References Cited

U.S. PATENT DOCUMENTS

| | | |
|---|---|---|
| 2,160,532 | 5/1939 | Barrett et al. |
| 3,284,385 | 11/1966 | D'Alelio |
| 3,654,251 | 4/1972 | D'Alelio |
| 3,809,712 | 5/1974 | Yetter ........................ 260/410.7 |
| 4,083,762 | 4/1978 | Krupp et al. ................. 204/181 R |
| 4,233,362 | 11/1980 | Novak et al. |
| 4,242,243 | 12/1980 | Antonelli et al. |
| 4,355,154 | 10/1982 | Saam et al. |
| 4,374,953 | 2/1983 | Chou et al. |
| 4,547,556 | 10/1985 | Hughes et al. |
| 5,648,518 | 7/1997 | Ritter et al. ..................... 560/224 |

FOREIGN PATENT DOCUMENTS

| | | |
|---|---|---|
| 2638544 | 6/1977 | Germany. |
| 60-221469 | 11/1985 | Japan. |

OTHER PUBLICATIONS

J.C. Padget, Journal of Coatings Technology, (1994) vol. 66 (839), p. 89.
Shlarb, et al., Progress in Organic Coatings, (1995) 26, 207.
J. March, Advanced Organic Chemistry, John Wile and Sons, New York, (1985), pp. 334, 348, 351.
A.H. Blatt, Organic Syntheses, vol. 2, Wiley and Sons, New York, (1943), p. 264.
S. Sussman, Ind. Eng. Chem., (1946) 38, 1228.
G.F. Vesley et al., J. Orig. Chem., (1971) 36, 2548.

*Primary Examiner*—Joseph L. Schofer
*Assistant Examiner*—Wu C. Cheng
*Attorney, Agent, or Firm*—Price, Heneveld, Cooper, DeWitt & Litton

[57] ABSTRACT

Glycol co-esters of drying-oil fatty acids and polymerizable unsaturated carboxylic acids are formed by a novel bi-phase catalysis in liquid-liquid or liquid-solid dispersions. The co-esters form directly from drying-oil acids and partial glycol esters of vinylic carboxylic acids, or vice versa. Complete removal of the by-produced water by distillation is unnecessary and the commonly encountered side reactions of direct esterification are suppressed since reaction temperatures can be as low as ambient. The expensive acid chlorides or anhydrides combined with acid acceptors, previously used to prepare such co-esters, are circumvented along with the by-produced hydrochlorides or carboxylates which must be recovered and disposed in an environmentally acceptable way. The co-esters formed here are useful in free radical copolymerizations that provide novel film-forming polymers capable of cross-linig when dried in air. They can be formed in bulk, solution or as latexes. When the carbinol-bearing structure of the co-ester is polymeric, novel polymers are produced having both pendant polymerizable vinyl carboxylate and drying-oil structures that rapidly air-cure at ambient temperature.

35 Claims, No Drawings

GLYCOL CO-ESTERS OF DRYING-OIL FATTY ACIDS AND VINYL CARBOXYLIC ACIDS MADE VIA BIPHASIC CATALYSIS AND RESULTING PRODUCTS

This application claims the benefit of U.S. Provisional Application No. 60/006,132, entitled "HYBRID GLYCOL ESTERS OF DRYING OIL FATTY ACIDS AND VINYL CARBOXYLIC ACIDS", filed Nov. 2, 1995; U.S. Provisional Application No. 06/007,798, entitled HYBRID GLYCOL ESTERS OF DRYING OIL FATTY ACIDS AND VINYL CARBOXYLIC ACIDS, filed Nov. 30, 1995; and U.S. Provisional Application No. 60/008,896, entitled HYBRID GLYCOL ESTERS OF DRYING OIL FATTY ACIDS AND VINYL CARBOXYLIC ACIDS, filed Dec. 19, 1995.

FIELD OF THE INVENTION

The present invention relates to drying-oil esters and their applications.

BACKGROUND OF THE INVENTION

Drying-oils are organic liquids which, when applied as a thin film, readily absorb oxygen from the air and polymerize to form a relatively tough, elastic film. Drying-oils are usually natural products from renewable resources such as linseed oil, tung oil, soybean oil, tall oil, dehydrated castor oil, and the like which are included as combinations of such natural oils or their fatty acids in various synthetic resins. The drying ability is due to the presence of unsaturated fatty acids, especially linoleic and linolenic, frequently in the form of glycerides but also as their corresponding carboxylic acids.

Alkyd resin-paints are a form of polyester used in coatings that are capable of oxidative-cure. They are made by condensation polymerization of dihydric or polyhydric alcohols, polybasic acids and a drying oil glyceride or acid. Typically the drying-oil glyceride form is converted to a monoglyceride, which is then reacted with an acid or acid anhydride to create an alkyd resin. When such resins are applied as coatings, the polymer backbones cross-link through polymerization of the drying-oil upon exposure to oxygen. The presence of trace amounts of certain metal salts, such as cobalt naptheneate, serve as catalysts to attain sufficiently rapid cure times. Very hard durable coatings are then formed. Alkyd resin paints are usually dispersed in solvent, but recently water dispersions have been developed. These are generally alkaline and suffer from hydrolysis of the polyester backbone and loss of properties during storage.

Solvent based alkyd resin paints form more durable coatings than latex paints and coatings since they are cross-linked, but latex coatings are easier to clean up in that they are water-based. Latexes comprise emulsions of polymeric materials in a continuous phase of water, having enough coalescing solvent to provide a continuous film on drying. They therefore are less environmentally damaging than the solvent-based alkyds. Further, since the polymer is in the discontinuous phase, significantly higher molecular weights than alkyds can be used without excessive increases in over-all viscosity. When latex paints are applied, they dry in place through evaporation of the water carrier and coalescing solvent, but they do not polymerize or cross-link in the drying process as in the alkyd resin oil-based paints, described above. When they are cross-linked, it is typically thermally in a separate stage using a hydroxy-functional copolymer latex mixed with melamines and acidic catalysts. This improves mechanical properties, rendering films solvent and water resistant. Lesser used two-package epoxy or urethane cures are also available, but one-package ambient air-cured latex systems similar to the alkyds are not in use.

J.C. Padget, *Journal of Coating Technology*, (1994), Vol. 66(839), page 89, reviews recent advances in emulsion technology beneficial to coating systems where differing mixtures of monomers are slowly fed sequentially to polymerizing emulsion mixtures. This produces emulsion particles having special morphologies which can impart improved stability and film-forming characteristics. The ensuing particle morphologies are sometimes referred to as "core-shell" emulsions while the polymerization technique is sometimes referred to as the "starved monomer" technique. Also reviewed therein are methods where pre-formed polymers with hydrophilic groups are dissolved in a water-soluble solvent, sometimes with a surfactant, and then dispersed in water. Under the proper conditions the solvent is then removed by distillation. The technique is especially useful for polymer systems unsuited for emulsion polymerization. Shlarb, et al., *Progress in Organic Coatings*, (1995) 6, 207, describe a variation of this method where two differing polymer compositions in solution, one rich in hydrophilic groups and the other deficient, are blended and then dispersed in water to produce emulsifier-free emulsions.

D'Alelio, in U.S. Pat. No. 3,284,385, discloses the preparation of an air-drying polymer comprising a co-ester having the following general formula:

$$R_dCO_2YO_2CC(R')=CH_2 \qquad (1)$$

where Y represents residuals of monomeric diols, triols, etc. and R' represents H and $CH_3$ and $R_d$ is a drying-oil unsaturated fatty chain. Polymers of these co-esters are made by a low temperature anionic polymerization in solution. However, co-esters with more than one copolymerizable unit are not disclosed and are purposely avoided. Nor does the patent disclose the use of free radical polymerization to achieve the desired copolymers since it was though that there might be copolymerization through the unsaturated groups in the fatty chain of the drying-oil acid. This would destroy the drying-oil entity. D'Alelio's approach is unsuitable for large-scale manufacturing since the co-esters are made using acid chlorides and glycol monoesters and voluminous amounts of amine hydrochloride salt are produced as by-products, creating a serious waste disposal problem. The disclosed transesterification also produces a volatile alcohol which must be disposed of in an environmentally acceptable way. Finally the disclosed transesterification can lead to extensive rearrangement of the desired ester structures through concurrent ester redistribution, leaving a mixture of all possible structures.

Tulacs, et al., German patent No. 2,638,544, prepare co-esters similar to D'Alelio's through the interaction of anhydrides of polymerizable carboxylic unsaturated acids with partial esters of drying-oil acids. The by-product was a polymerizable unsaturated acid, requiring its removal by distillation. The inventors also disclose emulsion copolymers with co-esters of Formula 1 where the monomer mixtures contain vinyl sulfate or phosphates for emulsion stability. The resulting emulsions, after formulating with pigments and a cobalt catalyst, gave hard, cross-linked films when dried in air at ambient temperature. The disclosed preparation of the co-ester having Formula 1, however, would be poorly suited for economic industrial practice because of the expense of recovering and disposing of the by-products.

Barrett and Strain, U.S. Pat. No. 2,160,532, also describe the preparation of co-esters of polyhydric alcohols with drying-oil acids having Formula 1 which are useful in coating compositions. Details are given of the preparation of products such as soybean oil diglyceride methacrylate, soybean oil monoglyceride dimethacrylate, coconut oil diglyceride methacrylate, China-wood oil diglyceride methacrylate, soybean oil monoglyceride monomethacrylate, and glycol laurate methacrylate. Such products may be used as coatings on steel, glass, or other surfaces, suitably with addition of a drier such as cobalt linoleate or in mixtures with resins, cellulose derivatives, etc. The acrylate co-esters are prepared by interaction of the glycerides with the corresponding acid chlorides of the alpha-methylene carboxylic acids. The by-produced hydrogen chloride and excess unreacted acid chloride are removed in vacuo, which in modern industrial practice would require recovery and suitable waste disposal.

Antonelli et al. in U.S. Pat. No. 4,242,243, produces high solids solvent-based coating compositions that dry in air comprising a backbone of polymerized monomers of styrene or methyl methacrylate, any alkyl acrylate and hydroxyl containing monomers such as hydroxyalkyl acrylate or hydroxyalkyl methacrylate and grafted pendant drying-oil fatty acid groups to provide compositions with ambient curing characteristics. Grafting is conducted with a minimum of xylene solvent using dibutyltin oxide catalyst at 190°–210°. By-produced water is removed by azeotropic distillation. At the high process temperatures used, extensive transesterification undoubtedly occurred, producing by-products such as methyl and glycol esters of the fatty acids along with unwanted carboxyl groups distributed along the backbone. For that reason, a post treatment of Cardura® oil (a glycidyl ester of a saturated aliphatic acid) was necessary to reduce the acid number. Depolymerization of the acrylic and methacrylic polymer backbones is also likely since process temperatures were well above the ceiling temperatures.

Novak et al., U.S. Pat. No. 4,233,362, disclose a polymer composition comprising a water-soluble salt or a polymer containing pendant groups derived from an unsaturated drying-oil fatty acid hydroxamide, carboxyl groups, carboxyl ester groups and optionally the residues of other unsaturated addition polymerizable monomers. Also disclosed are aqueous coating compositions in which the water-soluble polymer is either the sole polymeric vehicle or is combined with a water-insoluble polymer latex. The thermal grafting of the drying-oil fatty acid hydroxamide was conducted at temperatures somewhat lower than those of Antonelli's.

Hughs et al., U.S. Pat. No. 4,457,556, disclose a composition comprising a water reducible vinyl addition polymer having pendant unsaturated air-drying fatty acid ester groups and additional pendant groups selected from secondary amines, tertiary amines and combinations thereof which, when neutralized, can act as water solubilizers. This permits the preparation of aqueous dispersions suitable for cationic electrodeposition. The polymers are prepared by free radical copolymerization of a vinyl unsaturated monomer having Formula 1 with other vinyl unsaturated monomers. The copolymerization is achieved in a water miscible solvent and in the presence of a free radical source at 150° C. Such high temperatures can induce copolymerization or chain transfer with the unsaturated fatty acid structures and impair their air-drying ability. The electrodeposited films after drying were relatively soft, having 2b–4 b pencil hardness and gasoline resistance was poor to good. The unsaturated polymerizable co-ester having Formula 1 was claimed to be made from drying-oil fatty acids and partial glycol esters of acrylates and methacrylates. No method was taught, however, on how the problematic side reactions known to be encountered in typical esterifications were avoided, such as hydrolysis, acidolysis, alcoholysis or transesterification (See J. March, *Advanced Organic Chemistry*, John Wiley and Sons, New York, (1985) pp. 334, 348, 351).

Thus, there has been active interest in vinylic copolymers, in solution or water-based, whose cast films are capable of oxidatively air-drying and cross-linking at room temperature. Focus has been on copolymer systems with pendant fatty-acid drying-oil groups introduced by copolymerization of glycol co-esters of drying-oil fatty acids and acrylates or methacrylates. Such copolymers, in addition to offering the capability of oxidative air-cure at ambient temperature, also provide the important property of moisture resistance due to the long hydrophobic hydrocarbon chains. They also reduce critical film-forming temperatures. Of special interest are water-based coatings, including latex. A major barrier, however, has been lack of a economic means of producing the subject glycol co-esters of Formula 1 without producing troublesome by-products requiring expensive methods of recovery and waste disposal. Likewise, suitable copolymerization methods are required that do not destroy the unsaturated drying-oil structures through copolymerization or chain transfer. Also, the highly hydrophobic nature of $R_d$ in Formula 1, greatly reduces water solubility compared to the other monomers in emulsion polymerization. This causes special problems in emulsion polymerization, such as coagulation, and requires special adaptations.

Direct esterification between carbinols and carboxylic acids utilizes readily available raw materials and water is the only by-product, so recovery and waste disposal problems are minimal. Typically it is catalyzed by strong acids and is reversible. By-produced water is removed continuously by distillation or co-distillation with an organic solvent to favorably shift the equilibrium (See, for example A.H. Blatt, *Organic Syntheses* Vol. 2, Wiley and Sons, New York, (1943), page 264). This can lead to high temperatures, as seen in Antonelli et al., and consequently transesterification of the intended multiple ester structures can lead to a statistical distribution of products rather than a planned product. The temperature sensitive acrylate-drying oil acid co-esters of D'Alelio, Tulacs and Hughs (Formula 1) would therefore be subject to loss through uncontrolled polymerization as well as through transesterification in the conventional process. Direct esterifications are reported to be catalyzed by acidic ion exchange resins, but typically require removal of by-produced water by azeotropic distillation (S. Sussman, *Ind Eng. Chem.*, (1946) 38, 1228) or the presence of a drying agent (G.F. Vesley et al., *J Org. Chem.*, (1971) 36, 2548). These citations indicate the requirement for large excesses of carbinol to shift the equilibrium and none describe the formation of the co-esters given in Formula 1.

SUMMARY OF THE INVENTION

The present invention comprises the following aspects:

1. A bi-phasic method for producing glycol co-esters of polymerizable vinylic carboxylic acids and drying-oil carboxylic acids by esterification of partial glycol esters of polymerizable vinylic carboxylic acids with drying-oil carboxylic acids or, alternatively, partial glycol esters of drying-oil carboxylic acids with polymerizable vinyl carboxylic acids;

2. Using the drying-oil/vinyl acid co-esters, formed in the manner outlined in item 1, as monomers in copolymerizations of other vinyl monomers such as acrylic and methacrylic esters, styrene, substituted styrenes, vinyl carboxylate esters as vinyl acetate, methacrylic acid, etc. to create film-forming copolymer solutions or latexes that serve as oxidatively cured binders for coatings, inks, adhesive or sealants; and 3. Using drying-oils, formed in the manner outlined in 1, as reactive diluents in high solids paint binders, ink binders, adhesives or sealant binders.

The preferred embodiment encompasses:

1. A process for forming co-esters of a polyfunctional carbinol with air-drying fatty carboxylic acids having one or more double bonds and 10–24 carbon atoms and a second carboxylic acid having at least one polymerizible double bond wherein:
   a. the unsaturated fatty carboxylic acid having 10–24 carbon atoms interacts with a partial ester of a polyol and the unsaturated acid having a polymerizable double bond or;
   b. a partial ester of a polyol and an unsaturated fatty acid having 10–24 carbon atoms interacts with an unsaturated polymerizable carboxylic acid; and
   c. the process is conducted in water/oil inverse emulsion, microemulsion, or solid/liquid dispersion at 0°–100° C. catalyzed by the strongly acidic surfactants or sulfonated polymers including the cation exchange resins.

2. The compositions of item 1 and their polymerization products in bulk, solution, aqueous dispersion or emulsion.

3. Compositions in bulk, solution, or emulsion of item 1 where polymerizable unsaturated carboxylic acids and air-drying fatty unsaturated carboxylic acids having 10–24 carbon atoms are co-esterified with oligomeric or polymeric polyfinctional carbinols.

4. Non-polymeric liquid compositions of item 1 combined with the polymeric compositions of item 3 and solubilized together with 25% or less of a volatile cosolvent, and optionally in the presence of an activator or drying catalyst, wherein liquid films of such compositions laid out in air cause the polymeric and non-polymeric compositions to copolymerize and harden with minimal liberation of solvent fumes and air pollution.

5. Free-radical aqueous emulsion copolymers of item 1, where:
   a. the monomer feed includes glycol co-esters of polymerizable vinylic carboxylic acids with drying-oil fatty acids of item 1, partial glycol esters of polymerizable vinylic carboxylic acids or glycol co-esters of polymerizable vinylic carboxylic acids with drying-oil fatty acids of item 1 bearing hydroxyl groups, vinylic carboxylic acids, along with other emulsion polymerizable vinylic monomers; and
   b. optionally, where the polymerization is conducted in the "monomer starved" mode and where the mixture of monomers fed in the later stage of the copolymerization contains more of the vinylic carboxylic acid than the first stage of the copolymerization; and
   c. where the acidic groups in the product of a. are partly or completely neutralized subsequent to the polymerization.

6. Solutions of the copolymers of item 2 with other vinylic monomer units and 2–10% of a vinylic monomer having a water solubilizing hydrophilic group where the solutions are:
   a. dispersed in water and the non-aqueous part is removed partly or completely by distillation; and
   b. optionally, prior to the water dilution, copolymer solutions having different amounts of the hydrophilic solubizing group are blended.

7. Applications of the claimed compositions in coatings, inks, sealants, adhesives, rubbing oils, and reactive diluents.

DESCRIPTION OF THE PREFERRED EMBODIMENTS

The present invention concerns a biphasic method of preparing glycol co-esters of fatty drying-oil acids and unsaturated polymerizible carboxylic acids and their use as monomers in free radical copolymerizations. The co-esters have the general formula:

$$(R_dCO_2)_l(M)_mZX_n \qquad (2)$$

where $R_d$ represents structures with at least one double bond, but preferably more than one, and which are derived from the $C_{10}$–$C_{24}$ drying-oil acids such as eleostearoyl, linoleoyl, linolenoyl, oleoyl, arachidonoyl as single entities or in naturally occurring combinations that result from the processing of linseed oil, tung oil, soybean oil, menhaden oil, tall oil, dehydrated castor oil and the like. In these acids, or their naturally occurring ester derivatives, $R_d$ is capable of forming hydroperoxy structures upon exposure to air that subsequently cleave to RO● and HO● radicals when catalyzed by certain metal salts. Z is an aliphatic or aliphatic-aromatic hydrocarbyl or heterohydrocarbyl radical having l+m+n open valences where 1 and m each have a minimum value of one. X is hydroxy, acyloxy, halogen, alkoxy or carboalkoxy group, and n is zero or a positive integer. Illustrative of Z are:

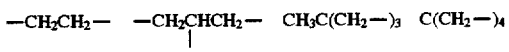

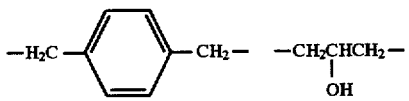

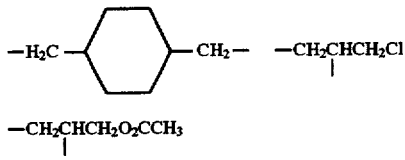

Z can also be polymeric or copolymeric as for example in carbinol-functional polyesters or in copolymers where the repeating units include such structures as:

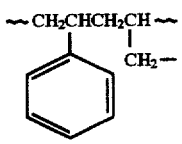

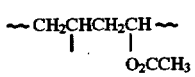

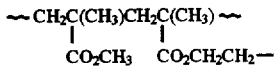

M represents an unsaturated moiety including at least one polymerizable carbon-carbon double bond and one or more carboxyl groups which link the unsaturated moiety (M) to radical Z. The unsaturated moiety M may also include various pendant groups which are free of polymerizable carbon-carbon double bonds such as hydrogen, alkyl, arylalkyl, aryl, chloroethyl, carboxy or carboxyester. Desirably, the unsaturated moiety (M) is the residue of an unsaturated carboxylic acid which has been linked to radical Z through one or more carboxylic groups via an esterification reaction. Suitable unsaturated carboxylic acids include those having one or more unsaturated carbon-carbon double bonds, and independently having one or more carboxylic groups. Specific examples include acrylic acid, methacrylic acid, α-haloacrylic acid, 2,4-pentadienoic acid, sorbic acid, maleic acid and itaconic acid as well as the partial esters of the dicarboxylic acids.

Illustrative examples of the co-esters produced by the biphasic method are:

are suppressed. The process can be represented schematically as

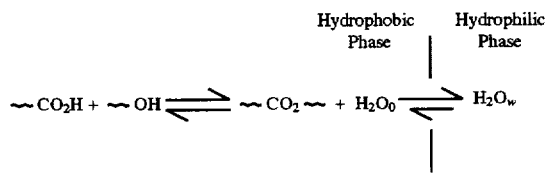

where $H_2O_0$ represents a small amount of water dissolved in the hydrophobic phase and $H_2O_w$ represents water dissolved in the hydrophilic phase.

The simplest form of catalyst that forms a separate liquid hydrophilic phase in inert hydrophobic media are the mineral acids, such as sulfuric acid, hydrochloric acid, perchloric acid, phosphoric acids (including from 85% to 100%

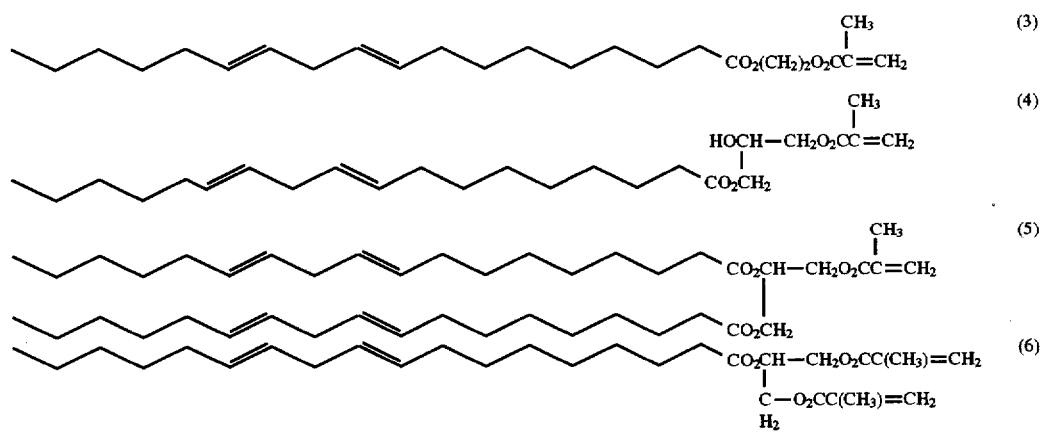

These may exist as single entities or as various mixtures.

The backbone of the polyolol, Z, may be oligomeric or polymeric with average molecular weights of 300 or greater. Examples of such polyols are polyester coating resins bearing carbinol-finctionality or various acrylic copolymers with glycol methacrylates. Yet other illustrative examples where Z is polymeric are the copolymers of styrene and allyl alcohol. The latter form co-esters of the formula:

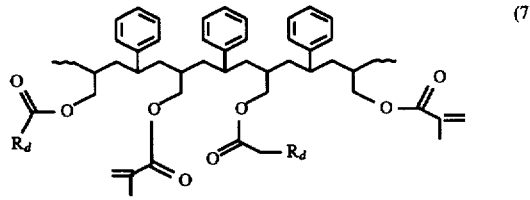

The biphasic process for esterification uses acidic catalysts that form a separate hydrophilic phase within an inert hydrophobic reaction medium that contains the carboxylic acid and carbinol. The system can be in the form of a liquid-in-liquid dispersion or solid in liquid dispersion. Examples would be a water-in-oil inverse emulsion or microemulsion where strongly acidic hydrophilic sites for example on a surfactant, concentrate in a discontinuous phase or microphase. The driving force for the process is a tendency for water formed in the esterification-hydrolysis equilibrium in the hydrophobic phase to transfer to the hydrophilic phase, thus shifting the equilibrium to the right. Proper choice of catalyst and reaction media permit esterifications at temperatures as low as ambient so that transesterification, ester exchange and other side-reactions orthophosphoric acid, metaphosphoric acid, and polyphosphoric acid), etc. More suitable catalysts, however, are strongly acidic surfactants that form inverse micelles with hydrophilic cores in hydrophobic media. Examples of such surfactants are the long chain alkanesulfonic acids, such as decylsulfonic acid, and the long chain alkyl-aromatic sulfonic acids such as dodecylbenzenesulfonic acid didodecyl-napthylenesulfonic acid or dodecyldiphenyloxidesulfonic acid. Non-ionic surfactants or cationic surfactants in combination with a mineral acid may also be used. The sulfonic acid surfactants are preferred and offer the convenience of serving as emulsifiers after neutralization in subsequent emulsion polymerizations.

Alternatively, the biphasic system can consist of liquid-solid dispersions in a hydrophobic medium where a solid phase, having hydrophilic characteristics, contains strongly acidic groups. Examples of one class of such solids are the sulfonated polystyrenes including the cross-lined sulfonated polystyrenes commonly used as cation exchange resins. Macroreticulated resins such as Amberlyst®-15 or Dowex® 50 strongly acidic cation exchange resins are especially useful. Another class of such solids is the poly (perfluorinated alkenes) having pendant sulfonic acid groups, such as Nafion-H®. Yet another class of such solids is the strongly acidic polyoxymetalates also known as heteropolyacids or metal oxide clusters. The acidic clays fall in this category. The strongly acidic cation exchange resins are especially preferred in that they are readily available and can easily be removed from the product by simple decanting or filtration without the requirement of neutralization to terminate the reaction. The recovered resins can optionally be reused in subsequent reactions.

The hydrophobic media which forms the other phase of the system, typically the continuous phase, may be composed of aliphatic, aliphatic-aromatic, aromatic or halogenated hydrocarbon diluents. The diluents are chosen so that the solubility of water is low and that the reactants are at least partly soluble. Examples are the hexanes, cyclohexane, toluene, the xylenes, benzene, chloroform and methylene chloride. In cases where the reactants are sufficiently hydrophobic, little or no diluent is required.

One group of carbinol functional reactants in the biphasic system have the general formula:

$$(HO)_l(M)_m ZX_n \qquad (8)$$

where Z, M, l, m and n have the definition previous set forth with respect to Formula 2. Typical examples would include ethylene glycol monomethacrylate, ethylene glycol monoacrylate, 1,4-butylene glycol monomethacrylate, acrylic mono and diglycerides, trimethylolpropane monomethacrylate and dimethacrylate, pentaerythritol trimethacrylate and 2-hydroxyethyl sorbate. These then interact with the drying-oil carboxylic acids bearing $R_d$ as defined in Formula 2. Examples are oleic acid, linoleic acid, linolenic acid, soya acid, linseed oil acid, tall oil acid, dehydrated castor oil acid and the like.

Another group of carbinol functional reactants for the biphasic system have the general formula:

$$(R_d CO_2)_l(OH)_m ZX_n \qquad (9)$$

where $R_d$, Z, l, m and n, and X have the definitions previously given for Formula 2. Typical examples would include 2-hydrodroxyethyl linoleate, linoleoyl mono and diglycerides, the mono and diglycerides of soya acids, linseed oil acids, tall oil acids, dehydrated castor oil acids and partial esters of linoleic acid and poly(styrene-co-allyl alcohol). These can then interact with unsaturated polymerizible acids of the general formula:

$$M(H)_p \qquad (10)$$

where M is defined in Formula 2 and p is one or more. Examples are acrylic, methacrylic, α-haloacrylic, 2,4-pentadienoic, sorbic, maleic and itaconic as well as the partial esters of the dicarboxylic acids.

The reaction can be run from the freezing point of the diluent to its boiling point, but is preferably from room temperature to 80° C., and reaction times can vary between a few hours to several days depending on temperatures and reactivities. It is beneficial to slowly flush the system with an inert gas such as nitrogen to suppress incidental oxidation and polymerization and to partly remove by-produced water. The method of terminating the reaction depends on the catalyst. Acidic surfactants are neutralized with bases such as ammonia, amines, hydroxides or bicarbonates, while the acidic solids and ion exchange resins are removed by decanting or filtration and can be reused. After termination, the diluents are optionally removed from the reaction mixture by evaporation at atmospheric pressure or in a vacuum depending on boiling point. Recovered diluents are optionally re-used in subsequent reactions. Volatile unreacted reagents that might be present in excess can also be optionally removed in a vacuum and reused. The residue is the product of Formula 2 and may be used without further purification or optionally distilled in a high vacuum, if possible.

Useful coatings, inks and sealants or adhesives form when monomers of Formula 2 participate in free-radical homopolymerizations or copolymerizations with other vinylic monomers. The polymerizations may be carried out in the absence of solvent (in bulk), in solution, or aqueous emulsion depending on the use intended. Thus, bulk polymerization would be preferred, for example, if a liquid composition containing Formula 2 were to be a solventless ink that is polymerized and cured in place. Still another application of bulk polymerization would be as reactive diluents in solventless coatings, sealant or adhesive formulations. Copolymers made with Formula 2 made in solution would be useful as a binder in traditional solvent-based coatings, high solids coatings or, depending on the nature of the diluent, as an intermediate stage in the preparation of water reducible coatings. Emulsion copolymers made with Formula 2 are useful in a range of applications including paints, inks, sealants and adhesives. The presence of monomer repeat units based on Formula 2 in these systems imparts the ability to cure oxidatively under ambient conditions to provide solvent and water resistance as well as reduced critical film-forming temperatures.

The composition of the disclosed emulsion polymers differs from that described in the prior art. The monomer composition here contains from 1–80% of monomers having the Formula 2, from 0.1–10% of a polymerizable carboxylic acid of general Formula 10, from 0.1% to 15% of polymerizable partial glycol esters of general Formula 8 or Formula 2 where X=OH, the balance being other polymerizable vinylic monomers such as acrylate or methacrylate esters of aliphatic or aromatic alcohols, styrene and substituted styrenes, vinyl acetate or other vinyl carboxylate esters, and a chain transfer agent which regulates molecular weight. The copolymerized carboxylic acid of general Formula 10, after being neutralized on completion of the polymerization, improves long-term emulsion stability. Monomers having the Formula 8 or Formula 2 where X=OH facilitate incorporation of the hydrophobic monomer, Formula 2 where OH is absent, by minimizing coagulation during polymerization. Other monomers serve to adjust film properties.

Methods of emulsion polymerization known to the art (See for example Padget and Tulacs et al.) are applied here with preference for a gradual feed of monomer to the polymerization and optionally with the monomer feed containing a greater portion of Formula 10 in the later stages of the polymerization. It is also preferred to conduct the polymerizations at temperatures as low as possible to prevent destruction or alteration of the drying-oil structures. This will be from ambient to 100° C., but preferably between 40° and 80° C. The emulsion copolymers are finally neutralized with basic hydroxides or amines to a final pH between 6 and 9. Neutralization improves emulsion stability by further preventing coagulation on storage.

EXAMPLE 1

This example illustrates how 2-methacryloxyethyl linoleate can form at room temperature as well as at 60° C. by the method of claim 1 via biphasic catalysis in a liquid-solid dispersion:

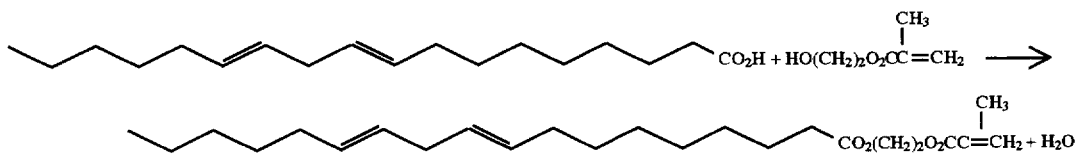

A suspension of 3.0 g of Amberlyst-15 in a solution of 6.0 g of linolenic acid (21.4 mmol), 3.5 g of 2-hydroxyethyl methacrylate (HEMA, 26.9 mmol) and 2 mg of 2.6-di-t-butyl-4-methylphenol (DTBMP) dissolved in 9.0 ml of dueterochloroform was stirred under nitrogen at room temperature (22°–23° C.) for 12 days. The suspension was filtered to give a clear solution which was washed several times to remove the excess HEMA which is water-soluble whereas linoleic acid and the product are water-insoluble. After drying over anhydrous sodium sulfate, the solution clarified and it was again filtered. A small sample of the solution was analyzed by $^{13}$C NMR while the remainder was kept under refrigeration. The $^{13}$C NMR was consistent with 2-methacryloxyethyl linoleate, (300 Mhz, in DCCl$_3$, TMS reference) δ(ppm): 172.9 (R$\underline{C}$O$_2$CH$_2$CH$_2$), 166.5 (CH$_2$=C (Me)$\underline{C}$O$_2$CH$_2$CH$_2$), 135.6 (cis $\underline{C}_{(9)}$=$\underline{C}_{(10)}$, linoleate), 127.7, 127.5 (cis $\underline{C}_{(12)}$=$\underline{C}_{(13)}$, (R CO$_2$$\underline{C}$H$_2$CH$_2$), 61.5 (CH$_2$=C (Me)CO$_2$$\underline{C}$H$_2$CH$_2$), 33.7 (CH$_{2(2)}$ linoleate), 29.2, 29.0, 28.8, 28.74, 28.71, ($\underline{C}$H$_{2(4-7)}$, $\underline{C}$H$_{2(15)}$linoleate), 26.8 (—$\underline{C}$H=CH—$\underline{C}$H$_{2(8)}$ linoleate), 25.3 ((—CH=CH)$_2$— $\underline{C}$H$_{2(10)}$, linoleate), 24.5 (CH$_{2(3)}$, linoleate), 22.2 (CH 17.8 (CH$_2$=C($\underline{C}$H$_3$)CO$_2$R), 13.6 (CH$_{3(18)}$, linoleate). Signals for the original reactants at (unreacted —$\underline{C}$O2H), 65.80 (unreacted $\underline{C}$H$_2$OH, unreacted HEMA) and 60.4 (CH$_2$=C (Me)CO$_2$$\underline{C}$H$_2$CH$_2$, unreacted HEMA) were either very weak or nonexisting and the ratio of the signal area intensity for methacrylate and linoleate CH$_3$ were nearly equal indicating a roughly 90% conversion.

Repeating the example but keeping the temperature at 63° C. and stirring for 21 hours rather than 12 days gave a material having the same $^{13}$C NMR at roughly 85% conversion.

EXAMPLE 2

This example illustrates how copolymers with the monomer described in the first example can be prepared by free radical copolymerization in solution. 2-methacryloxyethyl linoleate from the first example is copolymerized with methyl methacrylate and 2-hydroxyethyl monomethacrylate.

A solution of 1.0 g of 2-methacryloxyethyl linoleate from the first example where the solvent had been removed, 4.7 g of methyl methacrylate and 13.3 g of toluene was passed over a 1.0×1.0 column of activated Al$_2$O$_3$ to remove inhibitors and a light yellow color. Then 0.84 g of 2-hydroxyethyl monomethacrylate (HEMA) and 0.20 g of azobisisobutyronitrile were dissolved in 16.0 g of the eluate from the activated Al$_2$O$_3$ column. The clear colorless solution was placed in a vial with a magnetic stirrer, purged with nitrogen and sealed. The vial and contents were heated with stirring for 24 h at 70° C. in an oil bath. After this period, the viscosity of the still colorless solution increased to the point where the stirrer was no longer functional. The temperature was increased to 100° C. for 0.75 h to complete consumption of the initiator and monomers. The solution was then cooled to room temperature where it became extremely viscous.

A 1.0 g sample of the toluene solution was dispersed in with 10 ml of methanol at 55°–60° C. with stirring and cooled, whereupon the copolymer precipitated. The mass was separated from the supernatant solution and washed with methanol. The resulting dough-like residue was dried in vacuum at 50° C. whereupon it solidified. This procedure separated any unreacted monomers which are soluble in methanol while the copolymer is insoluble. The now solid sample was completely soluble in DCCl$_3$ or THF, and the solutions were respectively used for analysis by $^{13}$C NMR and gel phase chromatography (GPC).

$^{13}$C NMR (300 Mhz in DCCl$_3$, TMS reference, δ in ppm): 177.6(t) $\underline{C}$=O from polymerized methacrylate ester; 173.3 (s): $\underline{C}$=O from linoleate ester; 130.0(s), 129.8(s), 127.6(s): $\underline{C}$=$\underline{C}$ characteristic of unsaturation of linoleate; 66.6(s): $\underline{C}$H$_2$OC=O from polymerized 2linoleate; 60.2(s) from $\underline{C}$H$_2$OH in polymerized HEMA; 54.1(d, broad) —$\underline{C}$H$_2$, from methylene triads in methacrylic backbone; 51.6(s) $\underline{C}$H$_3$O pendant methoxy from polymerized methyl methacrylate; 44.5(t) from quaternary $\underline{C}$ triads in polymerized methacrylate; 34-22 (10 signals) from $\underline{C}$H$_2$ in the characteristic pattern of linoleate; 18.4, 16.2 (sh) $\underline{C}$H$_3$ methyl triads in polymerized methacrylate; 13.9(s) $\underline{C}$H$_3$ from terminal methyl in linoleate. The $^{13}$C NMR thus establishes incorporation of all the monomers into the copolymer. GPC (THF, polystyrene standards): M$_n$=4.1×10$^4$, M$_W$ 1.6×10$^5$.

The following illustrates that the copolymer undergoes cross-linking upon exposure to air. A 1.4 g sample of the viscous toluene solution of copolymer was blended with one drop of 6% cobalt napthenate and a 20 mil film of the solution was drawn down on a cold-rolled steel 3×5" panel. A clear tack-free film formed as soon as the toluene evaporated. (The clarity of the films indicates uniform copolymerization). After four days, the resulting 0.6 mil film was insoluble in acetone, gave a HB-F pencil hardness, and required 96 rubs with a diethyl ketone soaked cloth bound to a 24 oz. ball-peen hammer to wear through to the substrate. A noncross-linked copolymer of the same composition requires 15 rubs or less to wear through to the substrate.

EXAMPLE 3

This illustrates emulsion copolymerization of 2-methacryloxyethyl linoleate with methyl methacrylate and smaller amounts of HEMA and methacrylic acid.

An aqueous solution of 0.3 g of potassium persulfate, 2.5 g of 10% sodium dodecyl sulfosuccinate (Aerosol-OT), 2.5 g of 10% sodium dodecylbenzenesulfonate and 14 g of water was heated with stirring to 80° C. in an oil bath. The solution was in a 25 ml. two-necked flask equipped with a magnetic stirrer, reflux condenser, and a port for injecting monomer. Then, a mixture of 1.5 g of 2-methacryloxyethyl linoleate containing 26% HEMA, 3.0 g of methyl methacrylate, 0.2 g of methacrylic acid, and 0.2 g of dodecyl mercaptan (chain transfer agent) was slowly fed to the stirred aqueous solution at 80° C. through the port in ~0.5 ml increments over a period of 1.75 h. After the addition was complete, heating and stirring were continued for 3.5 h and the resulting high quality emulsion was cooled to room temperature with stirring. There was no indication of coagulation or coalescence. For analytical purposes, a 9.0 g sample of the emulsion was coagulated by adding ~1.5 ml of 10% aqueous magnesium sulfate and washing the coagulum three times with water followed by three times with methanol. The resulting mass was dissolved in ~10 ml of acetone, the traces of gel particles were filtered and the polymer was precipitated by adding the clear solution to excess petroleum ether. (Solutions of the polymer would not precipitate when added to excess methanol. The monomers including the 2-methacryloxyethyl linoleate were soluble in the acetone-petroleum ether but the polymer was insoluble.) The precipitation was repeated, and the resulting polymer was dried in a vacuum for 48 h. The polymer was then analyzed by $^{13}$C NMR and GPC.

The $^{13}$C NMR (300 Mhz in DCCl$_3$, TMS reference, δ in ppm) was essentially that of Example 2 except that the presence of carboxyl was indicated by a weak resonance at 178.3 ppm. Also, the CH$_2$ region was complicated by weak peaks due to the dodecyl mercaptan which had incorporated into the copolymer. GPC $M_n$=5.94×10$^3$, $M_w$=1.55×10$^4$.

Cast films of the emulsions were clear and hard but not cross-linked. Cross-linking was effected by neutralizing a 2 g sample of emulsion with 10% ammonium hydroxide and adding 2 drops of 12% Zr Hydrocure and 1 drop of Ca Hydrocure (commercial drying catalysts for water-based systems) and casting films. This produced acetone insoluble films after drying at room temperature for 24 h.

EXAMPLE 4

This example illustrates how an emulsion copolymer similar to that of Example 3 can be converted into an air-cured latex coating system having resistance to moisture and solvents. It illustrates that the 2-methacryloxyethyl linoleate monomer provides cross-linking as well as improved film-forming properties to a latex.

By following a procedure similar to Example 3, an emulsion polymer was prepared by slowly adding a miure of 1.34 g. of 2-methacryloxyethyl linoleate mixed with 0.16 g. of HEMA, 3.0 g. of methyl methacrylate, 0.2 g. of methacrylic acid and 0.027 g. dodecyl mercaptan to a stirred solution at 80° C. of 0.0235 g. of potassium persulfate, 0.94 g. of 10% sodium dodecylbenzenesulfonate, 0.94 g. of 10% Aerosol-OT® and 4.0 g. of water. The addition required 2⅔ h. Stirring continued at 80° C. for an additional 2 h and the mixture was cooled. The pH was adjusted to 7 with 10% ammonium hydroxide. This gave a somewhat viscous bluish emulsion which was stabile for 5 months in a sealed bottle. [After this period a thin skin had formed at the air-liquid interface that probably resulted from some oxidative cross-linking in the oil phase through the linoleate groups. Very little coagulation was noted.]

A mixture of 2.0 g. of the emulsion, 0.2 g. of 2-butoxyethanol, 1 drop of 12% zirconium hydrocure and 1 drop of % 5 calcium hydrocure was drawn-down as a 10 mil film on a 3×5" aluminum panel. After drying the formulated latex 2 h. at room temperature in static air, the film was clear, colorless and tack free. A small piece of film cut from the panel at this point was insoluble in acetone [a good solvent for uncross-linked acrylic polymers] indicating that it was already substantially cross-linked. After 20 h. at room temperature the film hardened to a B pencil hardness and to HB hardness after 42 h. At this point the film was resistant to both diethyl ketone and water. After 7 days at room temperature the film hardened to H pencil hardness and required 40 rubs under the weight of a 24 ox ball-peen hammer having a diethyl ketone soaked cloth bound to its hemisphere in order to wear through to the substrate. In a similar test with a water soaked cloth there was no wear-through after 150 rubs where the test was discontinued.

Comparative Example 4

This shows that there is no cross-linking and that the film-forming properties are poor when 2-methacryloxyethyl linoleate is excluded from Example 4.

An emulsion polymer was prepared following the same procedure as Example 4 but where the scale is larger while maintaining the same weight ratios of ingredients and omitting the 2-methacryloxyethyl linoleate. Thus, a solution of 21.4 g. of methyl methacrylate, 1.1 g. of HEMA, 1.4 g. of methacrylic acid and 0.191 g. dodecyl mercaptan was slowly fed to a stirred solution at 80° C. of 0.134 g. of potassium persulfate, 5.3 g. of 10% sodium dodecylbenzenesulfonate, 5.3 g. of 10% Aerosol-OT® and 22.7 g. of water. The addition required 1.5 h. after which the stirring was continued at 80° C. for an additional 2.5 h. This gave a bluish stabile emulsion of 41% solids that was essentially free of coagulum.

The emulsion, 5.0 g., was diluted with 1.2 g. water to adjust the solids level and 0.62 g. of 2-butoxyethanol, 2 drops of 12% zirconium hydrocure and 2 drops of 5% calcium hydrocure were added with stirring. A portion was drawn down as a 10 mil film on a 3×5" aluminum panel and dried at room temperature. After 2 h. the water had essentially evaporated leaving polymer, but not a film. In contrast with the film of Example 4, the discontinuous residue was brittle, flaked and was unsuitable as a coating. Film properties could not be evaluated. A sample of the residue was completely soluble in acetone indicating the absence of a cure.

EXAMPLE 5

A mixture of soya mono- and diglycerides, prepared by transesterification of soybean oil with glycerol, is converted to the acrylate co-ester having Formula 2 where Z is glyceryl unit by a biphasic catalysis in a liquid-solid dispersion.

A mixture of 82.6 g. of soybean oil (est. 94.5 meq of ester), 17.4 g. of glycerol (189 mmol) and 1.0 ml of 21% sodium ethoxide in ethanol (3.1 meq) was purged with nitrogen while being stirred, heated to 240° C. and held there for one hour. After cooling to room temperature, still under nitrogen, the system was neutralized with carbon dioxide (dry ice) and any precipitated solids were removed by filtration and centrifugation. The resulting clear oil was completely soluble in methanol whereas the original mixture of soybean oil and glycerol was hazy and insoluble in methanol. The $^{13}$C NMR indicated the product was a mixture of mono- and diglycerides with the 1-mono glyceride and the 1,3-diglyceride being the major components. The table lists signals in the $^{13}$C NMR (300 MHz, in DCCl$_3$, TMS reference, δ in ppm) for the new ester and carbinol structures:

| Structure | Ester C=O | R$_4$CO$_2$CH$_2$ | R$_4$CO$_2$CH | CH$_2$CH | CHOH |
| --- | --- | --- | --- | --- | --- |
| 1-mono-glyceride | 174.0 (s) | 64.9 (s) | — | 63.2 (s) | 70.0 (s) |
| 2-mono-glyceride | 174.0 | — | 74.6 (w) | 62.2 (w) | — |
| 1,2-diglyceride | 173.3 (1, w) 173.6 (2, w) | 61.0 (w) | 62.0 (w) | 72.2 (w) | — |
| 1,3-diglyceride | 173.7 (s) | 64.8 (s) | — | — | 67.9 (s) |

-continued

| Structure | Ester C=O | R$_d$CO$_2$CH$_2$ | R$_d$CO$_2$CH | CH$_2$CH | CHOH |
|---|---|---|---|---|---|
| triglyceride | 173.1 (1, w) 172.7 (2, w) | 62.1 (w) | 68.8 (w) | — | — |

[(s): strong signal, (w): weak to very weak signal, (1 or 2): the position on the glyceride chain where the ester C=O is located.]

Other major signals in the $^{13}$C NMR were a group of two envelopes corresponding to unsaturation in the fatty acid structures (127.7–128.1 and 129.5–130.0 ppm), a broad envelope corresponding to the methylene units in the fatty acid structures (22.0–34.0 ppm) and a cluster corresponding to the terminal methyl groups in the fatty acid structures (13.6–14.1 ppm).

A solution of 10.0 g. of the monoglyceride mixture (est. 28.2 mmol), 2.03 g of acrylic acid (28.2 mmol) and 2 mg of 2,6-di tert. butyl-4-methylphenol in 10 ml of hexane was stirred with 3.00 g of Amberlyst®-15 cation exchange resin at room temperature for 7 days. The resin beads and a small amount of gel that had formed were separated from the solution by decantation followed by filtration. The solution was washed three times with saturated sodium sulfate (to suppress a tendency for emulsification) and then dried over anhydrous sodium sulfate. The majority of the hexane was evaporated at room temperature in a stream of nitrogen and finally in a vacuum at room temperature to give a light brown oil which was stored in the refrigerator to prevent spontaneous gelation.

A $^{13}$C NMR of a sample indicated that the 1-monoglyceride originally present had reacted to form an acrylate co-ester since the strong C=O ester signal at 174 ppm from the 1-monoglyceride had vanished along with its strong CH$_2$OH, CHOH and RCO$_2$CH$_2$ signals at 63.2, 64.9 and 70 ppm respectively. These were replaced with a new distinctive signal corresponding unambiguously to acrylate ester C=O at 169.5 ppm and slightly shifted and intensified signals at 68.0 and 64.8 ppm corresponding to the CHOH and RCO$_2$CH$_2$ in a new 1,3-diglyceride. Weak signals at 62.1 and 68.7 indicated partial conversion of the 1,3-diglyceride to a new triglyceride. Other major signals corresponding to C=C, methylene and methyl were essentially unchanged from the original mixture of mono- and diglycerides. The strong C=C signals from the unsaturation in the glycerides masked the C=C of the new acrylate structure.

EXAMPLE 6

This illustrates how a polymeric glycol co-ester of methacrylic acid and linoleic acid (Z in Formula 2 is polymeric) is prepared by a biphasic catalysis in a liquid-liquid dispersion and where the catalytic phase consists of inverse micelles.

A solution of 11.75 g. of poly(styrene-co-allyl alcohol) containing 7.7% OH (53.2 meq. of CH$_2$OH) in 27 ml of toluene (18.5 g) was prepared by warming and stirring the mixture in a 100 ml 3-necked flask equipped with a magnetic stirrer thermometer, nitrogen inlet and a Dean-Stark trap attached to a reflux condenser. After the polymer dissolved 6.7 g of linoleic acid (23.9 mmol) and 1.7 g. of dodecylbenzenesulphonic acid (DBSA), (5.2 mmol) were added with stirring and the temperature was adjusted to 60° C. under a purge of 13 cc/min of nitrogen. The dispersion was clear and nearly colorless but showed a strong Tyndall effect in a columnated beam of white light indicating a microemulsion or micelles. After 18 h at 60° C. 0.2 ml of water had collected in the Dean-Stark trap. The mixture was cooled to 40° C. and 2.52 g. of methacrylic acid (23.9 mmol) was added. The mixture was kept at 40° C. under a nitrogen sweep of 13 cc/mil for an additional 24 hr., then cooled to room temperature and kept under nitrogen.

A portion of the product was precipitated from a 3.5 g. sample by adding slowly to 100 ml of stirred methanol. The supernatant methanol was decanted, the viscous precipitate was then vigorously stirred with 100 ml of methanol and, the methanol was decanted. Washing with methanol was repeated and the residual methanol was removed from the viscous precipitate in a vacuum at room temperature. The dried product, which was a light brown clear, tacky semi-solid, was kept under nitrogen.

All the original components, the poly(styrene-co-allyl alcohol), linoleic acid, methacrylic acid, and the DBSA are completely soluble in methanol. Therefore the semi-solid is poly(styrene-co-allyl alcohol) that has been rendered methanol-insoluble through esterification with linoleic and methacrylic acids. This is substantiated by the $^{13}$C NMR spectrum (run as in previous examples) with signals at 145.2 ppm, 128.0 ppm and 125.6 ppm from monosubstituted aromatic in poly(styrene-co-allyl alcohol), 40.3 ppm from CH$_2$ in poly(styrene-co-allyl alcohol). In addition to the signals characteristic of linoleate were present (see Examples 1 and 2). The C=C signal from methacrylate at 125.7 ppm was partly masked by the stronger aromatic signals, but its presence was apparent from other characteristic signals at 167.3 ppm (methacrylate C=O), at 136.3 ppm (C=CMeCO$_2$R) and at 18.2 ppm (C-CMeCO$_2$R).

A 2.0 g. sample of the reaction mixture was mixed with 3 drops of 6% cobalt napthenate, drawn-down as a 5-mil film on a 3×5" aluminum panel and dried at room temperature. Within 5 hours the clear film was tack-free and gave a HB pencil hardness and within 24 hours. Surprisingly, without the cobalt napthenate a similar film was also tack-free within 5 hours giving a 7B pencil hardness and within 24 hours a HB pencil hardness.

It will be apparent to those skilled in the art that various modifications to the preferred embodiment of the invention as described herein can be made without departing from the spirit or scope of the invention as defined by the appended claims.

The embodiments of the invention in which an exclusive property or privilege is claimed are defined as follows:

1. A method for preparing co-esters of polymerizable vinylic carboxylic acids and unsaturated fatty carboxylic acids, comprising:

forming a hydrophobic phase containing a polymerizable vinylic carboxylic acid and a partial ester of a polyol and an unsaturated fatty carboxylic acid;

forming a hydrophilic phase containing an acidic catalyst;

contacting the hydrophobic phase and the hydrophilic phase under conditions sufficient to form a biphasic system in which the hydrophobic phase is continuous and the hydrophilic phase is dispersed within the continuous hydrophobic phase and under conditions sufficient to cause an acid catalyzed esterification reaction between the polymerizable vinylic carboxylic acid and the partial ester of a polyol and an unsaturated fatty carboxylic acid.

2. The method of claim 1, wherein the unsaturated fatty carboxylic acid has from about 10 to about 24 carbon atoms.

3. The method of claim 2, wherein the hydrophobic phase and the hydrophilic phase are contacted at a temperature of from about 0° C. to about 100° C.

4. The method of claim 3, wherein the acidic catalyst includes an acidic surfactant or a sulfonated polymer.

5. The method of claim 3, wherein the acidic catalyst is a mineral acid.

6. The method of claim 5, wherein the mineral acid is selected from sulfuric acid, phosphoric acids, hydrochloric acid and perchloric acid.

7. The method of claim 3, wherein the acidic catalyst is a long chain alkane sulfonic acid.

8. The method of claim 3, wherein the acidic catalyst is a long chain alkyl-aromatic sulfonic acid.

9. The method of claim 3, wherein the acidic catalyst includes a cationic exchange resin.

10. The method of claim 9, wherein the cationic exchange resin is a cross-linked sulfonated polystyrene or a poly(perfluorinated alkene) having product sulfonic acid groups.

11. The method of claim 3, wherein the hydrophilic and hydrophobic phases are contacted to form a water-in-oil inverse emulsion, a microemulsion, or a solid in liquid dispersion.

12. The method of claim 1, wherein the hydrophobic phase further contains at least one partial ester of an oligomeric or polymeric polyfunctional carbinol with an unsaturated fatty carboxylic acid, and wherein the hydrophobic phase and the hydrophilic phases are contacted under conditions sufficient to cause an acid catalyzed esterification reaction between the polymerizable vinylic carboxylic acid and the partial ester of the oligomeric polyfunctional carbinol with the unsaturated fatty carboxylic acid.

13. The method of claim 1, wherein the polymerizable vinylic carboxylic acid is selected from acrylate acid, methacrylic acid, a-haloacrylic acid, 2,4-pentadienoic acid, sorbic acid, maleic acid, itaconic acid and partial esters thereof.

14. The method of claim 13, wherein the unsaturated fatty carboxylic acid is selected from oleic acid, linoleic acid, linolenic acid, soya acids, linseed oil acids, tall oil acids, and dehydrated castor oil acids.

15. A method for preparing co-esters of polymerizable vinylic carboxylic acid and unsaturated fatty carboxylic acid, comprising:
   forming a hydrophobic phase containing an unsaturated fatty carboxylic acid and a partial ester of a polyol and an unsaturated acid having a polymerizable double bond;
   forming a hydrophilic phase containing an acidic catalyst;
   contacting the hydrophobic phase and the hydrophilic phase under conditions sufficient to form a biphasic system in which the hydrophobic phase is continuous and the hydrophilic phase is dispersed within the continuous hydrophobic phase, and under conditions sufficient to cause an acid catalyzed esterification reaction between the unsaturated fatty carboxylic acid and the partial ester of a polyol and an unsaturated acid having a polymerizable double bond.

16. The method of claim 15, wherein the unsaturated fatty carboxylic acid has from about 10 to about 24 carbon atoms.

17. The method of claim 16, wherein the hydrophobic phase and the hydrophilic phase are contacted at a temperature of from about 0° C. to about 100° C.

18. The method of claim 17, wherein the acidic catalyst includes an acidic surfactant or a sulfonated polymer.

19. The method of claim 17, wherein the acidic catalyst is a mineral acid.

20. The method of claim 19, wherein the mineral acid is selected from sulfuric acid, phosphoric acids, hydrochloric acid and perchloric acid.

21. The method of claim 17, wherein the acidic catalyst is a long chain alkane sulfonic acid or a poly(perfluorinated alkene) having pendant sulfonic acid groups.

22. The method of claim 17, wherein the acidic catalyst is a long chain alkyl-aromatic sulfonic acid.

23. The method of claim 17, wherein the acidic catalyst includes a cationic exchange resin.

24. The method of claim 23, wherein the cationic exchange resin is a cross-linked sulfonated polystyrene.

25. The method of claim 17, wherein the hydrophilic and hydrophobic phases are contacted to form a water-in-oil inverse emulsion, a microemulsion, or a solid in liquid dispersion.

26. The method of claim 15, wherein the hydrophobic phase further contains at least one partial ester of an oligomeric or polymeric polyfunctional carbinol with an unsaturated acid having a polymerizable double bond, and wherein the hydrophobic phase and the hydrophilic phase are contacted under conditions sufficient to cause an acid catalyzed esterification reaction between the unsaturated fatty carboxylic acid and the partial ester of the oligomeric or polymeric with polyol an unsaturated acid having a polymerizable double bond.

27. The method of claim 15, wherein the unsaturated acid having a polymerizable double bond is acrylic acid, methacrylic acid, α-haloacrylic acid, 2,4-pentadienoic acid, sorbic acid, maleic acid, itaconic acid and partial esters thereof.

28. The method of claim 27, wherein the unsaturated fatty carboxylic acid is selected from oleic acid, linoleic acid, linolenic acid, soya acids, linseed oil acids, tall oil acids, and dehydrated castor oil acids.

29. A method for preparing a co-ester of a polymerizable vinylic carboxylic acid and an unsaturated fatty carboxylic acid, comprising:
   forming a hydrophobic phase containing a carbinol functional reactant having one of the general formulas

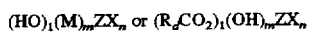

$$(HO)_l(M)_m ZX_n \text{ or } (R_dCO_2)_l(OH)_m ZX_n$$

where Z is an aliphatic or aliphatic-aromatic hydrocaryl or heterohydrocarbyl radical having l+m+n open valences, l and m are integers having a minimum value of 1, and n may be 0 or a positive integer, X is an hydroxyl, an acyloxy, a halogen, an alkoxy or a carboalkoxy group, and M is an unsaturated moiety including at least one polymerizable carbon-carbon double bond, $R_d$ represents structures with at least one double bond and which are derived from a drying-oil acid; an unsaturated carboxylic acid, said unsaturated carboxylic acid being an unsaturated fatty carboxylic acid if the carbinol functional reactant is free of $R_d$ groups;

forming a hydrophilic phase containing an acidic catalyst; and contacting the hydrophobic phase and the hydrophilic phase under conditions sufficient to form a biphasic system in which the hydrophobic phase is continuous and the hydrophilic phase is dispersed within the continuous hydrophobic phase, and under conditions sufficient to cause an acid catalyzed esterification reaction between the compound represented by Formula 8 and the unsaturated fatty carboxylic acid, and between the compounds represent by Formulas 9 and 10.

30. The method of claim 29, wherein the compound of Formula 8 is selected from ethylene glycol, monomethacrylate, ethylene glycol monoacrylate, 1,4-butylene glycol monomethacrylate, and acrylic monoglyceride, and acrylic diglyceride, trimethylolpropane monomethacrylate, trimethylolpropane dimethacrylate, pentaerythritol trimethacrylate and 2-hydroxyethyl sorbate.

31. The method of claim 30, wherein the unsaturated fatty carboxylic acid has from about 10 to about 24 carbon atoms.

32. The method of claim 31, wherein the unsaturated fatty carboxylic acid is selected from oleic acid, linoleic acid, linolenic acid, a soya acid, a linseed oil acid, a tall oil acid, and a dehydrated castor oil acid.

33. The method of claim 29, wherein the compound represented by Formula 9 is selected from partial esters of a polyol and an unsaturated fatty carboxylic acid having from about 10 to about 24 carbon atoms.

34. The method of claim 33, wherein the unsaturated fatty carboxylic acid is oleic acid, linoleic acid, linolenic acid, a soya acid, a linseed oil acid, a tall oil acid, and a dehydrated castor oil acid.

35. The method of claim 33, wherein the compound represented by Formula 10 is selected from acrylic acid, methacrylic acid, α-haloacrylic acid, 2,4-pentadienoic acid, sorbic acid, maleic acid, itaconic acid, and partial esters thereof.

* * * * *

UNITED STATES PATENT AND TRADEMARK OFFICE
CERTIFICATE OF CORRECTION

PATENT NO. : 5,750,751
DATED : May 12, 1998
INVENTOR(S) : John C. Saam

It is certified that error appears in the above-identified patent and that said Letters Patent is hereby corrected as shown below:

On the title page item [57],

Abstract, Line 16;

"cross-linig" should be --cross-linking--.

Column 2, Line 39;

"though" should be --thought--.

Column 3, Line 52;

"wate:r" should be --water--.

Column 3, Line 66;

"2b-4 b" should be --2b-4b--.

Column 4, Line 21;

"a" should be --an--.

Column 5, Line 34;

"polyfinctional" should be --polyfunctional--.

Column 6, Lines 2-3;

"solubizing" should be --solubilizing--.

Column 7, Line 41;

"carbinol-finctionality" should be --carbinol-functionality.

Column 9, Line 24;

"defmed" should be --defined--.

UNITED STATES PATENT AND TRADEMARK OFFICE
CERTIFICATE OF CORRECTION

PATENT NO. : 5,750,751
DATED : May 12, 1998
INVENTOR(S) : John C. Saam

It is certified that error appears in the above-identified patent and that said Letters Patent is hereby corrected as shown below:

Column 10, Line 55;

"fmal" should be --final--.

Column 10, Line 57;

"furither" should be --further--.

Column 11, Line 25;

After "135.6" insert -- $(CH_2=C(Me)CO_2R)$, 129.6, 129.5 --.

Column 11, Line 26;

After "127.5(cis$\underline{C}_{(12)}=\underline{C}_{(13)}$," insert --linoleate), 125.4 ($\underline{C}H_2=C(Me)CO_2R$), 62.1--.

Column 11, Line 27;

After "33.7($\underline{C}H_{2(2)}$ linoleate)," insert -- 31.2 ($CH_{2(16)}$, linoleate) , --.

Column 11, Line 29;

"(-CH=CH-$\underline{C}H_{2(8)}$" should be --(-CH=CH-$\underline{C}H_{2(8\&14)}$,--.

Column 11, Lines 30;

After "22.2(CH" insert -- $_{2(17)}$, linoleate), --.

Column 11, Line 32;

"(unreacted -CO2H)," should be --177.8 (unreacted -$\underline{C}O_2H$),--.

UNITED STATES PATENT AND TRADEMARK OFFICE
CERTIFICATE OF CORRECTION

PATENT NO.  : 5,750,751
DATED       : May 12, 1998
INVENTOR(S) : John C. Saam

It is certified that error appears in the above-identified patent and that said Letters Patent is hereby corrected as shown below:

Column 12, Line 23;

"2linoleate" should be --2-methacryloxyethyl linoleate--.

Column 12, Line 24;

"$\underline{C}H_2OH$" should be --$\underline{C}H_2OH$--.

Column 13, Line 37;

"miure" should be --mixture--.

Column 13, Line 54;

"%5" should be --5%--.

Column 14, Line 59;

$R_dCO_2\underline{C}H_2$   $R_dCO_2\underline{C}H$ should be -- $R_dCO_2\underline{C}H_2$   $R_dCO_2\underline{C}H$--.

Column 15, Line 17;

"28.2 mmnol)" should be --(28.2 mmol)--.

Column 15, Line 17;

"(28.2 nunol)" should be --(28.2 mmol)--.

Column 16, Lines 1-2;

"(23.9 mmnol)" should be --(23.9 mmol)--.

UNITED STATES PATENT AND TRADEMARK OFFICE
CERTIFICATE OF CORRECTION

PATENT NO. : 5,750,751
DATED : May 12, 1998
INVENTOR(S) : John C. Saam

It is certified that error appears in the above-identified patent and that said Letters Patent is hereby corrected as shown below:

Column 16, Line 3;

"cc/mil" should be --cc/min--.

Column 17, Claim 13, Line 30;

"a-haloacrylic" should be --α-haloacrylic--.

Signed and Sealed this

Eighth Day of December, 1998

Attest:

BRUCE LEHMAN

Attesting Officer

Commissioner of Patents and Trademarks